United States Patent [19]

Chang

[11] Patent Number: 5,246,448
[45] Date of Patent: Sep. 21, 1993

[54] METHOD AND APPARATUS FOR STEREOTACTIC TRAJECTORY SPECIFICATION

[75] Inventor: Hsuan Chang, Clifton Park, N.Y.

[73] Assignee: General Electric Company, Schenectady, N.Y.

[21] Appl. No.: 883,736

[22] Filed: May 15, 1992

[51] Int. Cl.[5] .......................................... A61B 19/00
[52] U.S. Cl. ..................................... 606/130; 606/1; 128/653.5
[58] Field of Search .................. 606/1, 130; 604/116; 128/653.1-653.5

[56] References Cited

U.S. PATENT DOCUMENTS

| | | | |
|---|---|---|---|
| 3,073,310 | 1/1963 | Mocarski | 606/130 |
| 3,817,249 | 6/1974 | Nicholson | 606/130 |
| 4,463,758 | 8/1984 | Patil et al. | 606/130 |
| 4,618,978 | 10/1986 | Cosman | 606/130 |
| 5,050,608 | 9/1991 | Watanabe et al. | 606/130 |

FOREIGN PATENT DOCUMENTS

| | | | |
|---|---|---|---|
| 1206116 | 12/1965 | Fed. Rep. of Germany | 606/130 |
| 1047472 | 10/1983 | U.S.S.R. | 606/130 |
| 1055504 | 11/1983 | U.S.S.R. | 606/130 |
| 1342478 | 10/1987 | U.S.S.R. | 606/130 |

OTHER PUBLICATIONS

"A New Computerized Tomographic-Aided Robotic Stereotaxis System", Y. S. Kwoh; Robotics Age, vol. 7, Issue 6 pp. 17-21, 1985.
An Articuluted Neurosurgical Navigation System Using MRI an dCT Images, IEEE Trans. on Biomedical Engineering, Y. Kosugi et al. vol. 35 Issue 2, pp. 147-151, 1988.
Neurosurgery, (edited by Wilkins & Rengachary), McGraw-Hill Book Co. pp. 2465-2489 1985.
"Tumor Stereotaxis", Patrick J. Kelly, M.D., 1991, pp. 1-50 (chapter 1: Introduction and Historical Aspects) (Chapter 2: Stereotactic Instruments).
"Sterotactic Neurosurgery", Robert L. Galloway and Robert J. Maciunas, Critical Reviews in Biomedical Engineering, vol. 18, Issue 3, 1990, pp. 181-205.

Primary Examiner—Stephen C. Pellegrino
Assistant Examiner—Glenn K. Dawson
Attorney, Agent, or Firm—Paul R. Webb, II

[57] ABSTRACT

The specification of a trajectory for performing a stereotactic medical procedure uses a phantom having a simulated target and a simulated incision point. The simulated target is placed in a position corresponding to the target within a patient and the simulated incision point is placed in a position corresponding to the planned incision point on the patient. A passive positioner is placed such that a surgical tool supported thereon extends through the simulated incision point and to the simulated target. The passive positioner is then secured so as to maintain its orientation. The positioner may then be moved to adjacent the patient for performing the actual medical procedure on the patient. Alternately, a second positioner, constructed identically to the first positioner, is adjusted to have the same settings as established by use of the simulated target and simulated incision point.

20 Claims, 8 Drawing Sheets

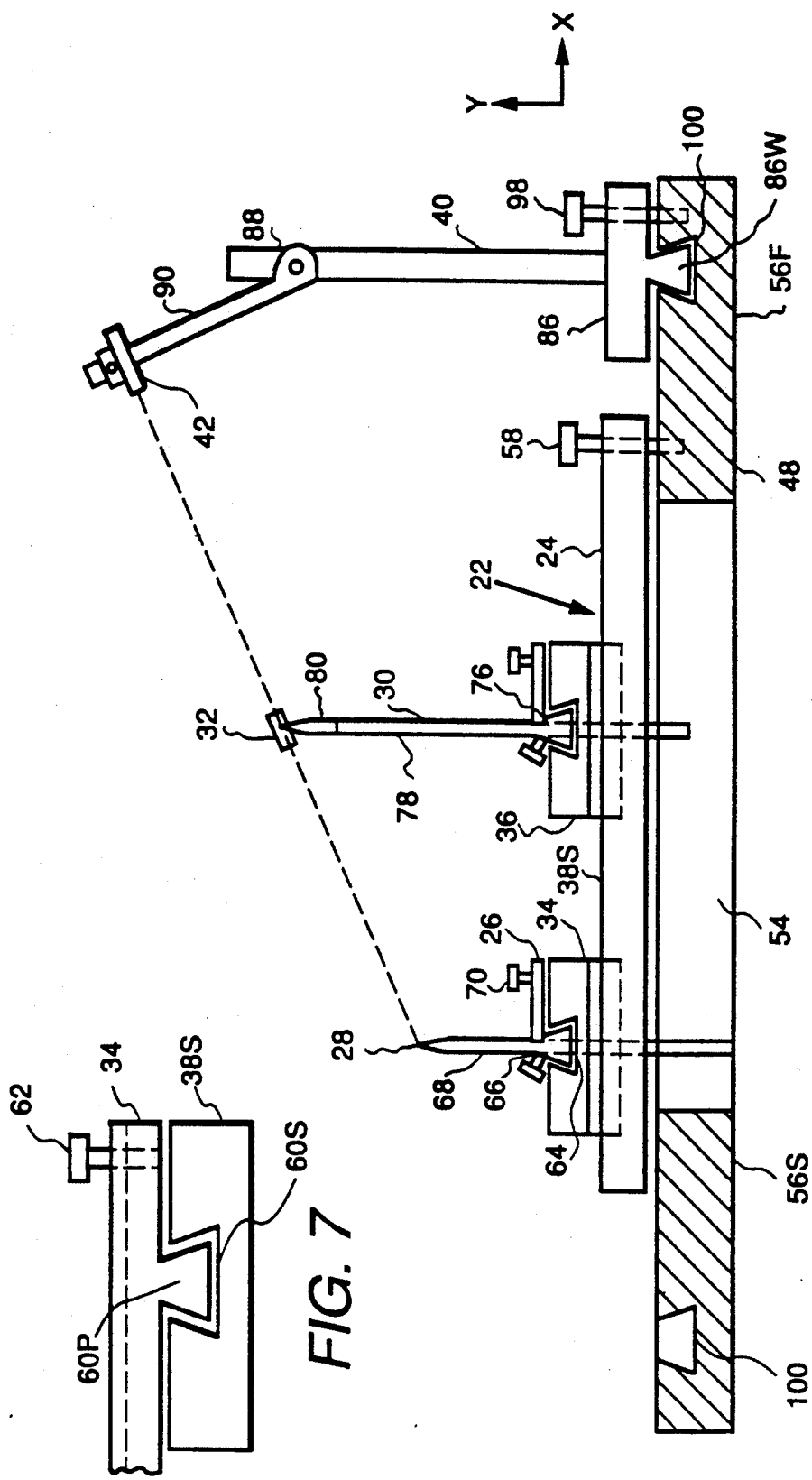

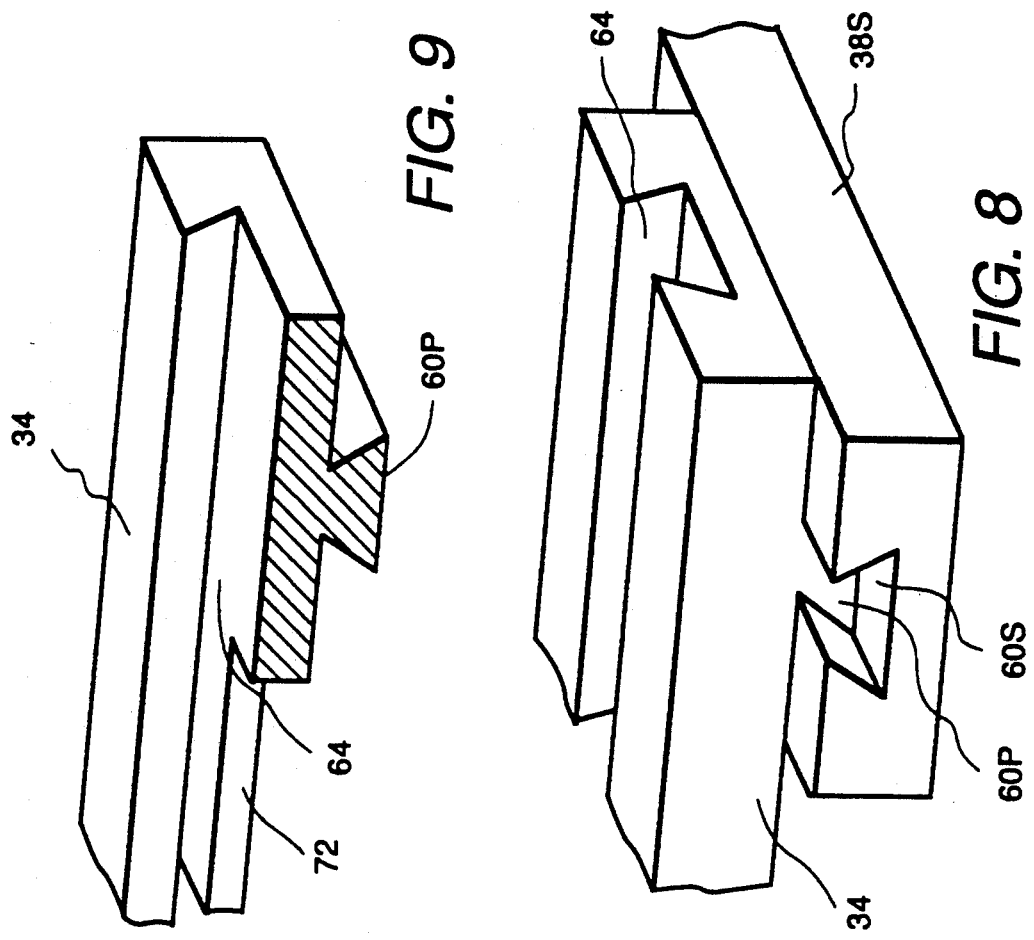
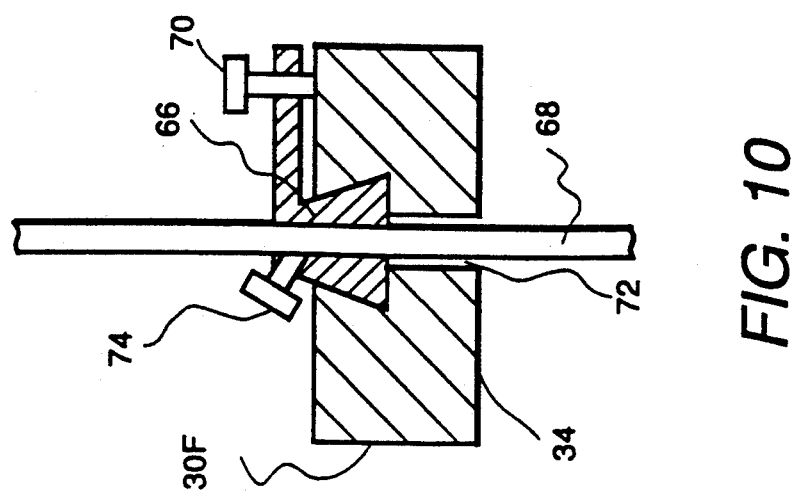

METHOD AND APPARATUS FOR STEREOTACTIC TRAJECTORY SPECIFICATION

CROSS REFERENCE TO RELATED APPLICATION

This application relates to copending application Ser. No. 07/883,741, filed concurrently herewith and assigned to the same assignee as the present invention.

BACKGROUND OF THE INVENTION

This invention relates to stereotactic trajectory specification for use in medical procedures.

When performing various medical procedures, it is necessary to insure that a surgical tool placed within the patient is accurately positioned. For example, a surgeon may be using a needle to take a biopsy of a brain tumor. The surgeon must be certain that the needle is accurately placed within the patient's brain in order to take the biopsy. Whether a surgeon is taking a biopsy or treating a patient by trying to kill tumor cells using a surgical tool, accurate placement is necessary to minimize any damage to healthy brain tissue. The calculations necessary to insure that the surgical tool has the proper trajectory are difficult and non-linear, which may lead to inaccuracies. Determining the accuracy of the calculations is accomplished by a technique which is somewhat incomplete.

Traditional stereotactic systems, such as the popular BRW frame illustrated in FIG. 1, employ a number of arcs to achieve the number of degrees of freedom needed to access a given target in three dimensional space. The frame 10 of FIG. 1 includes various mechanical adjustable parts or numerical control elements allowing one to define different trajectories. The degrees of freedom of the BRW frame of FIG. 1 are indicated by the parameters alpha, beta, delta, and gamma.

When a surgeon wishes to perform a medical procedure upon a target within a patient, the patient is placed upon an operating table and the patient (or at least the portion of the patient, such as the head, upon which the procedure is to be performed) is secured against movement relative to a particular frame of reference. Imaging techniques are used to locate the target zone, such as a tumor, within the patient. After the surgeon locates the target using the imaging system, such as computed tomography (CT), the surgeon selects an incision point in the patient. The incision point, which would be on the patient's skull when performing a medical procedure on the brain of a patient, corresponds to the place where the surgical tool will enter the patient. The incision point is selected by the physician so as to minimize damage to the patient's healthy tissues and/or so as to avoid any critical structures within the patient.

Having determined the location of the target and the incision point within the patient, nonlinear calculations are performed so as to give the proper values for alpha, beta, delta, and gamma as to provide the proper trajectory so that a surgical tool may access the target within the patient by going through the incision point. Upon setting the numerical control elements of the BRW frame of FIG. 1 by adjustment of fasteners, such as thumb screws, the frame 10 is moved to a phantom 12 as shown in prior art FIG. 2. The phantom 12 has a carriage 14 mounted for movement along tracks or rods extending in two perpendicular directions. Mounted to the carriage 14 is a target rod 16 having a target point 18 disposed thereon. The target point or portion 18 is placed in a position such that it corresponds to the location of the actual target within the patient. This is done by moving the carriage 14 along the tracks extending in perpendicular directions and by having an arrangement to vertically adjust the target portion or tip 18. A surgical tool such as a needle 20 is placed within a corresponding holder of the frame 10. If the needle does not intersect the target portion 18, either the settings on the frame 10 or the positioning of the target portion 18 are improper. In the usual case, the needle 20 will intersect the target portion 18 and the depth of insertion of the needle 20 in order to reach target portion 18 is marked on the needle so that this depth of insertion may be duplicated when actually operating on the patient.

Having confirmed the accurate settings on the frame 10 by using the phantom 12, the surgeon or assisting medical personnel will remove the frame 10 and attached it to a base ring (not shown) secured to the patient and corresponding to the frame of reference used for the target identification. The needle 20, which was removed from frame 10 when frame 10 was attached to the base ring, is then extended through the needle holder to the proper depth and the tip of the needle would be at the target within the patient's brain or other part of his body.

More details with respect to the prior techniques for stereotactic trajectory specification are described in Robert L. Galloway et al., Stereotactic Neurosurgery, CRC Reviews in Biomedical Engineering, 18(3):207-233 (1990) and chapters 1 and 2 of Tumor Stereotaxis by Patrick J. Kelly, copyright 1991 W. B. Saunders Company.

Although the various trajectory specification techniques previously used such as the BRW frame and the improved CRW frame have allowed surgeons to locate targets within patients, they have been subject to one or more of several disadvantages. They have required non-linear calculations to determine parameters which do not have an easy intuitive relationship with the x, y, and z coordinates of the target and the incision point which may be developed from the imaging system. In other words, it is not easy to see the relationship between, for example, the beta parameter for the frame of FIG. 1 and the x coordinate of a target within the patient. Note that, if the target is a tumor or other structure having a sufficiently large volume, the surgical tool may have to be placed at several different parts of the tumor or other target zone. For each of these placements, one would require the non-linear and relatively non-intuitive calculations. Each non-linear calculation is a potential source of positional inaccuracy. A second disadvantage of the prior art technique is that the testing arrangement shown in FIG. 2 simply determines that the tip of the needle will be disposed at the target. However, the testing arrangement of FIG. 2 does not insure that the needle 20 goes through the desired incision point. Although minor various from the proper incision point may be acceptable in some situations, deviation from the proper incision point under other situations could cause the needle 20 to damage critical structures within the patient or to otherwise damage healthy tissue more than is necessary.

OBJECTS AND SUMMARY OF THE INVENTION

Accordingly, it is a primary object of the present invention to provide improved stereotactic trajectory specification.

A more specific object of the present invention is to provide an apparatus for stereotactic trajectory specification which allows for testing a stereotactic trajectory to insure that its incision point, as well as its target, is proper.

A further object of the present invention is to provide for stereotactic medical procedures with a reduced need for making calculations, especially a reduced need for making non-linear and/or relatively non-intuitive calculations.

Yet another object of the present invention is to provide for convenient and improved accuracy stereotactic medical procedures.

A still further object of the present invention is to provide a method for checking the incision point and target of a proposed stereotactic trajectory.

The above and other objects of the present invention are realized by an apparatus for use in stereotactic medical procedures having a phantom. The phantom has a base defining a plane in which perpendicular x and z axes are disposed, a target simulator, and an incision simulator. The target simulator is movably positionable at different x, z locations on the base and has a target portion which is securable at different y locations along a y axis extending perpendicular to the plane, the x, y, and z axes being orthogonal. The incision simulator is movably mounted to the base for positioning at different x, z locations on the base and has a member with an incision portion thereon. The incision portion is securable at different y locations. The incision portion further has a pivot defining a simulated incision point therein. The pivot is mounted for independent rotation about perpendicular first and second pivot axes. The pivot is rotatable about the first and second pivot axes without changing the x, y, and z coordinates of the simulated incision point. The pivot accommodates a surgical tool therein such that the surgical tool may extend through the pivot to the target portion for determining the proper positioning of the surgical tool for a stereotactic medical procedure. Preferably, the first pivot axis is perpendicular to the plane and the second pivot axis is parallel to the plane.

The target simulator includes a target carriage mounted to the base for track movement along the x and z axes and the incision simulator includes an incision carriage for track movement along the x and z axes. The base includes at least one x track extending in the x axis and two z tracks extending in the z axis. The two z tracks are slidably mounted to the x track. The target carriage and incision carriage are slidably mounted to separate ones of the two z tracks.

The apparatus further includes a first positioner adjacent to the phantom and having a surgical tool holder. The surgical tool holder has a plurality of degrees of freedom. The surgical tool holder is securable to dispose the first positioner in an operation position whereat the surgical tool holder holds a surgical tool so that it extends from the surgical tool holder through the pivot to the target portion. The first positioner is passive.

The apparatus may further include a phantom table having a positioner receiver thereon. The phantom is mounted to the phantom table and the first positioner is mounted to the positioner receiver of the phantom table. The apparatus may further include a patient table adjacent the phantom and having a positioner receiver thereon. The positioner receiver of the patient table and the positioner receiver of the phantom table each have indicia adjacent thereto to allow duplication of positioner placement on the patient table and phantom table. The surgical tool holder of the positioner includes a tube portion rotatable about two perpendicular tube axes. The pivot and the tube portion are both cylindrical.

The method of the present invention is a method for stereotactic medical procedures including positioning a target simulator of a phantom at an $X_t$, $Z_t$ location relative to a base of the phantom,, the base defining a plane in which perpendicular x and z axes are disposed. A target portion of the target simulator is secured at a $Y_t$ location corresponding to a y axis extending perpendicular to the plane and where $X_t$, $Y_t$, $Z_t$ correspond respectively to coordinates along the x, y, and z axes of a target within a patient. An incision simulator of the phantom is positioned at an $x_i$, $z_i$ location relative to the base of the phantom. An incision portion on a member of the incision simulator is secured at a $Y_i$ location. The coordinates $X_i$, $Y_i$, and $Z_i$ correspond respectively to coordinates along the x, y, and z axes of a planned incision point on a patient. The incision portion has a pivot defining a simulated incision point therein and the pivot is mounted for independent rotation about perpendicular first and second pivot axes. A surgical tool is placed within the pivot. (As used herein, this surgical tool may be an actual surgical tool, such as a needle, used to operate on a patient or may be a simulated surgical tool having characteristics, such as shape and/or size to conform to an actual surgical tool which would be used on the patient.) The pivot is then rotated about at least one of the fist and second pivot axes such that a tip of the surgical tool touches the target. The pivot is rotatable about the first and second pivot axes without changing the x, y, z coordinates of the simulated incision point.

The method may further include placing a first positioner adjacent the phantom, the first positioner having a surgical tool holder with the surgical tool disposed therein. The surgical tool holder has a plurality of degrees of freedom. The rotating of the pivot is performed with the surgical tool in the pivot and in the surgical tool holder to dispose the surgical tool holder in an operation position whereat the surgical tool holder holds the surgical tool so that it extends from the surgical tool holder through the pivot to the target portion. The first positioner is secured in the operation position. The phantom is secured to a phantom table having a z track extending in the x axis. The placing of the first positioner adjacent the phantom is accomplished by securing the first positioner along the z track in the phantom table. The securing of the first positioner in its operation position is accomplished by securing a plurality of fasteners, each fastener securing the surgical tool holder against movement relative to at least one of the degrees of freedom.

A first method according to the present invention includes moving the first positioner from adjacent the phantom to adjacent the patient with the surgical tool holder remaining in the operation position. The medical procedure is then performed on the patient with the surgical tool holder determining the incision point and target on the patient respectively corresponding to $X_i$, $Y_i$, $Z_i$ and $X_t$, $Y_t$, $Z_t$. A tube portion of the surgical tool holder of the first positioner is rotated about at least one tube axis when rotating the pivot. More specifically, the tube portion is rotated about two perpendicular tube axes when rotating the pivot. The first and second pivot axes about which the pivot is rotated are respectively perpendicular to the plane and parallel to the plane.

A second method according to the present invention includes the placing of a second positioner having a surgical tool holder adjacent a patient with the second positioner in an operation position dependent on the operation position determined by use of the first positioner. The medical procedure is then performed on the patient with the surgical tool holder of the second positioner determining the incision point and target on the patient respectively corresponding to $X_i$, $Y_i$, $Z_i$ and $X_t$, $Y_t$, $Z_t$. This method further includes determining a plurality of settings on the first positioner when it is in its operation position and securing the second position in its operation position such that it has the same settings as determined from the first positioner.

The positioning of the target simulator is accomplished by x track movement and z track movement of the target simulator, meaning that movement in the x direction is along a track and movement in the z direction is along a track. Further, the positioning movement and z track movement of the incision simulator.

BRIEF DESCRIPTION OF THE DRAWINGS

The above and other features of the present invention will be more readily understood when the following detailed description is considered in conjunction with the accompanying drawings wherein like characters represent like parts throughout the several views and in which:

FIG. 6 is a view of a phantom table and associated parts looking in the same direction of view as with FIG. 5;

FIG. 7 is a simplified side view, with portions broken away, of a part of the components shown in FIG. 6;

FIG. 8 is a perspective view of two of the tracks illustrated as part of the structure shown in FIG. 6;

FIG. 9 is a partial cross section view with a portion broken away of a part of one of the tracks illustrated in FIG. 8;

FIG. 10 is a cross section view of the track of FIG. 9, taken perpendicular to the lengthwise direction of the track;

DETAILED DESCRIPTION

Figure 3:
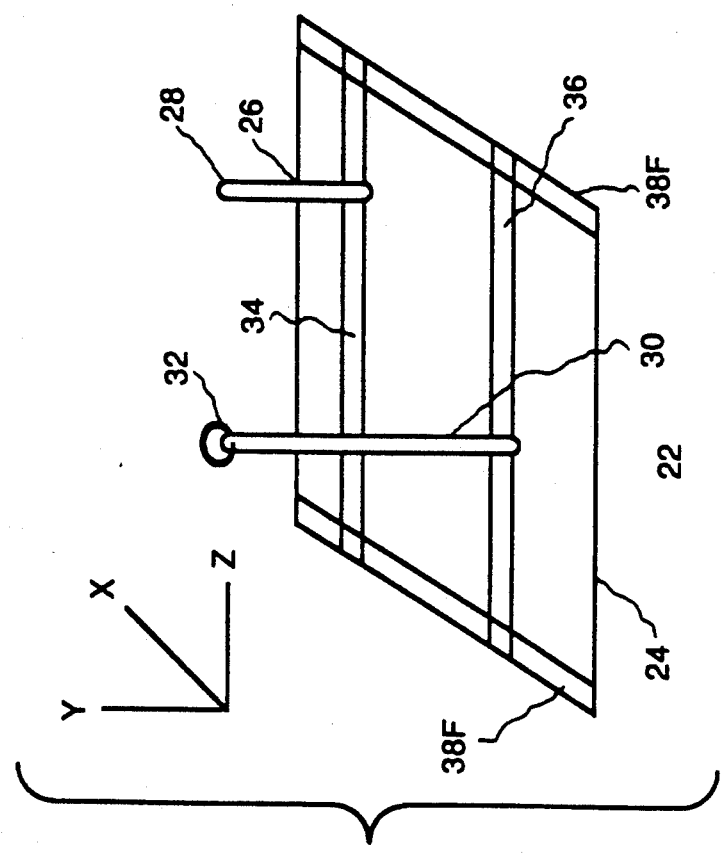
FIG. 3 is a perspective view showing the concept of the phantom according to the present invention.

Turning initially to FIG. 3, a phantom 22 according to the present invention is shown in very simplified form. The phantom 22 has a base 24 which supports a target simulator 26 having a target portion 28 at its tip. The target portion 28 is securable at different x, y, z coordinates (see the illustrated coordinate system) with the target simulator 26 supported by the base 24. the base 24 further supports an incision simulator 30 having an incision pivot 32, serving as an incision portion, disposed at its end. The incision pivot 32 may be placed at various x, y, z coordinates such that the path from the incision pivot 32 to the target 28 defines a stereotactic trajectory which one wishes to use for a particular patient.

The target simulator 26 would be placed at a point $X_t$, $Y_t$, $Z_t$ corresponding to the actual target upon a patient. the incision pivot 32 would be placed at a point $X_i$, $Y_i$, $Z_i$, corresponding to a planned incision point on the patient. The incision pivot 32 may be a sleeve as discussed below, but could alternately be a ring or any other shape which will accommodate a surgical tool by holding it to the simulated incision point. The correspondence is that the target portion 28 and incision pivot 32 have coordinates relative to a phantom frame of reference which are identical (or at least linearly related) to the coordinates of the actual target within the patient and the planned incision point on the patient relative to a patient frame of reference as will be explained in more detail below.

The base 24 allows calibrated (using indicia) movement of the target simulator 26 and incision simulator 30 in a plane corresponding to the x and z axes. Additionally, the target simulator 26 and incision simulator 30 have arrangements to respectively allow calibrated (using indicia) movement of the target portion and incision pivot 32 in the y axis. The details of these various arrangements to allow movement of the target portion 28 and incision pivot 32 will be discussed below, but it will briefly be noted that FIG. 3 schematically illustrates use of a z target track 34 extending in the z axis to allow z movements of the target simulator 26 and a z incision track 36 extending along the z axis to allow z movement of the incision simulator 30. Each of the z tracks 34 and 36 are mounted to allow sliding movement along parallel first and second x tracks 38F and 38S which extend along the x axis.

Figure 2:
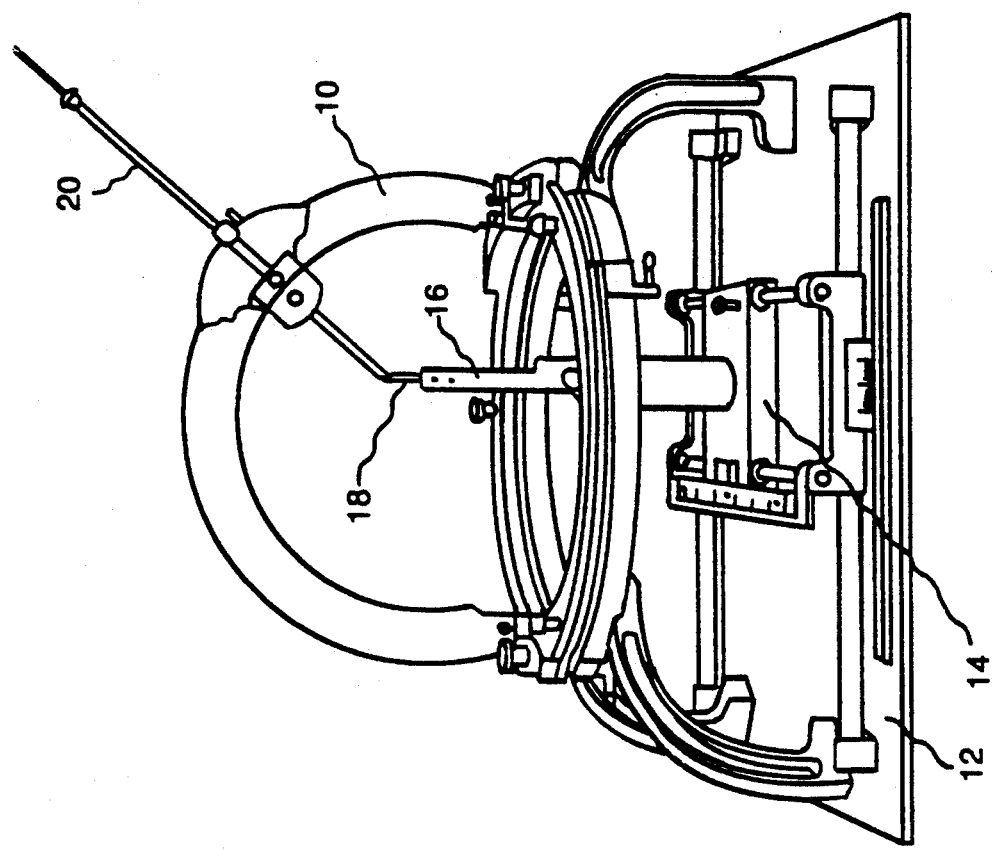
FIG. 2 is a perspective view of the prior art frame on FIG. 1 attached to a prior art phantom as discussed above.
Figure 1:
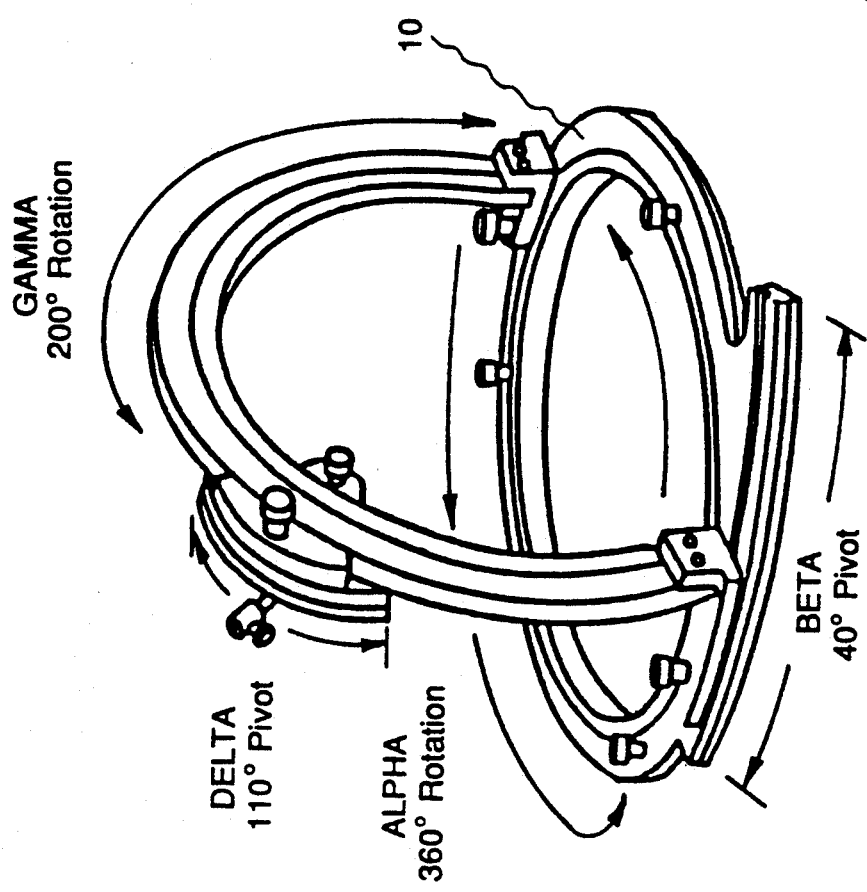
FIG. 1 is a simplified perspective view of a prior art frame as discussed above.
Figure 4:
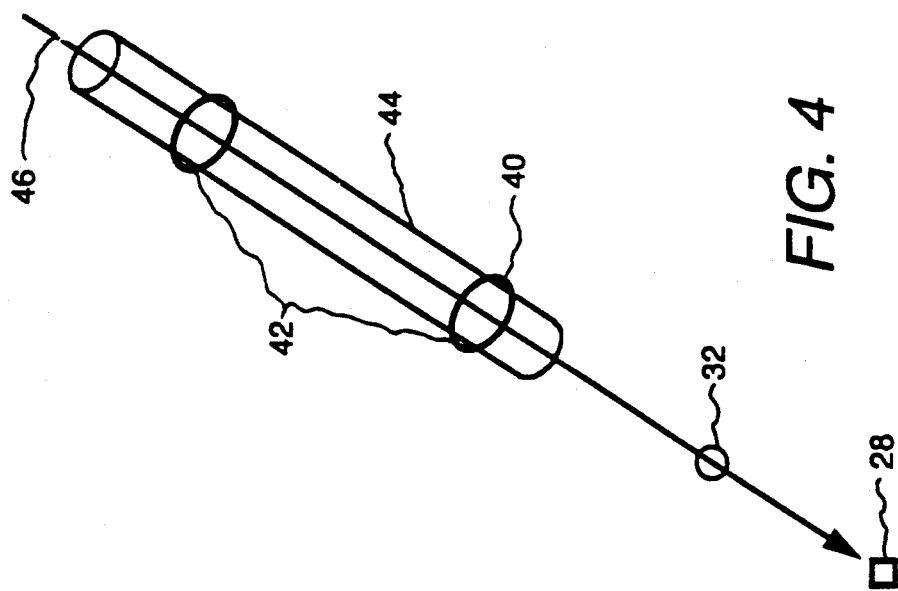
FIG. 4 is a simplified perspective illustrating how the phantom of the present invention may interact with a positioner according to the present invention.

A principle of operation of the present invention will be discussed with reference to the highly simplified schematic of FIG. 4. A mechanical positioner is simply shown as including two rings which constitute a tubular portion 42 and which serves as a surgical tool holder to hold a cannula or needle holder 44. The portion 42 holds a needle 46 by way of the needle holder 44. Upon the target portion 28 and incision pivot 32 being disposed int he proper coordinates as discussed above, the positioner 40 is brought adjacent to the incision pivot 32 and the needle 46 is placed within the needle holder 44 so as to extend through the incision pivot 32. The positioner 40 is moved until the needle 46 extends through incision pivot 32 so as to touch the target portion 28. The positioned 40 would then be considered to be in its operation position and it would be locked in that position. The needle 46 would be marked to indicate the depth of insertion within needle holder 44 so as to reach the target portion 28. The positioner 40 would then be moved to adjacent the patient. Since the positioner 40 is oriented and located relative to the actual target within the patient corresponding to its orientation and previous position relative to the target portion 28 of target simulator 26, the needle 46 could be applied to the actual patient and it would act on the proper target within the patient. Further, one would have a higher degree of confidence that the incision point on the patient would be proper than in the case of prior art FIG. 2 wherein the phantom tests the target, but does not confirm that the trajectory passes the planned incision point.

Figure 5:
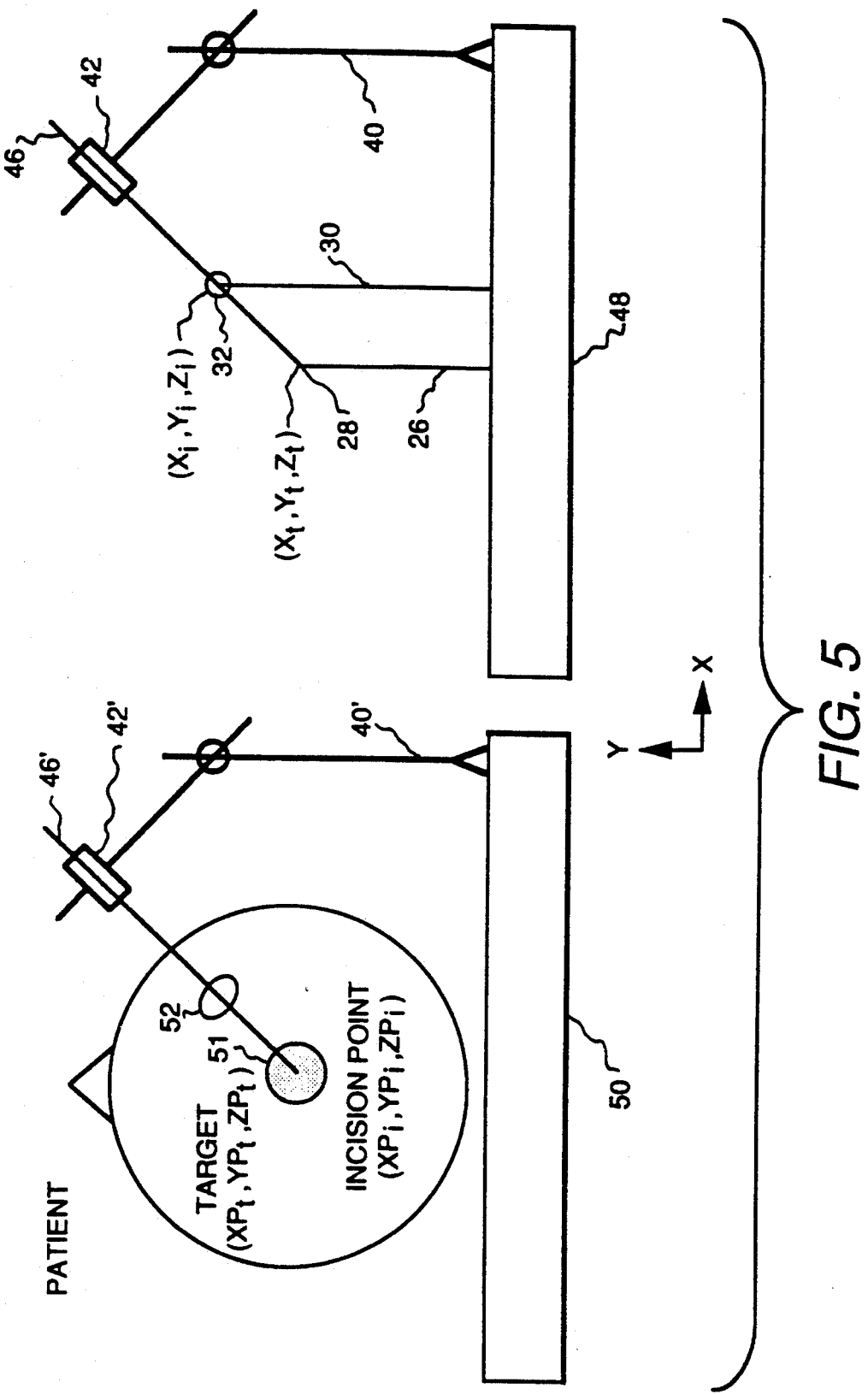
FIG. 5 shows a simplified view of the apparatus of the present invention looking along the length of a patient (i.e., from the patient's head towards his feet)

The simplified illustration of FIG. 5 will help further explain the present invention. A phantom table 48 is disposed adjacent (not necessarily as close as shown) a patient table 50 upon which a patient is secured. The phantom table 48, which is only schematically illustrated in FIG. 5, allows one to simulate the target and incision point of the patient by use of the target simulator 26 and incision simulator 30. For simplicity, the base 24 of phantom 22 of FIG. 3 is not shown in FIG. 5. In practice, it would be attached to the phantom table 48 or the phantom table 48 would incorporate the base 24 as a portion thereof. A first positioner 40, illustrated schematically, is movably mounted to the table 48 and includes the tubular portion 42.

As shown at the left side of FIG. 5, the target 41 would be identified at point $XP_t$, $YP_t$, $ZP_t$, each of these values being coordinates relative to a patient frame of reference. Depending upon the size of the target, it may be necessary or advisable to identify more than one point corresponding to the target. In addition to determining the coordinates of target 51 using standard techniques such as a known imaging system, the coordinates of an incision point 52 relative to the patient frame of reference will be determined after the surgeon has decided where the incision point should be. Next, the target portion 28 and incision pivot 32 are secured at locations corresponding respectively to the target 51 and incision point 52. In the simplest and most preferably case, the coordinates of target portion 28 and incision pivot 32 relative to a phantom frame of reference will be identical respectively to the coordinates of the target 51 and incision point 52 relative to the patient frame of reference. Thus, $X_t$ is equal to $XP_t$, $Y_t$ is equal to $YP_t$, etc. The positioner 40 is secured at an appropriate location on the phantom table 48 such that the needle 46 may be placed through the tubular portion 42 and through the incision pivot 32. The incision pivot 32 may pivot about two independent axes, one which is parallel to the lengthwise direction of target simulator 30 and another which is perpendicular to that lengthwise direction. The details of the pivot 32 will be discussed below. However, once the needle 46 is placed to extend through tubular portion 42 and the incision pivot 32, the incision pivot 32 may pivot about its two axes without changing the x, y, and z coordinates of the simulated incision point defined by the incision pivot 32. The incision pivot 32 is pivoted about one or both of its axes by using the needle 46 so that the needle 46 lines up through the incision pivot 32 to the target portion 28. The surgeon or other medical personnel marks the needle 46 to indicate how far it should be inserted into the tubular portion 42 or a needle holder mounted thereon (not separately shown in FIG. 5). When the needle 46 extends through the incision pivot 32 to the target portion 28, the positioner 40 will be secured in its position relative to numerous degrees of freedom which it normally would have.

Following the securing of positioner 40 in its operation position, a first alternative for using this information to determine the stereotactic trajectory will now be discussed. In this first technique, positioner 40 would have various indicia on it (not shown in FIG. 5) and the medical personnel would read off the indicia. A second positioner 40' having tubular portion 42' would be secured to the patient table 50 at a location corresponding to the location at which 40 was disposed upon the phantom table 48. In other words, the positioner 40' would have a base (not separately shown in FIG. 5) which is secured to a position on table 50 having the same coordinates in the patient frame of reference as the base (not shown) of the first positioner 40 relative to the phantom frame of reference. Using the simple example where the coordinates of corresponding points in the patient frame of reference are equal to the coordinates of corresponding points in the phantom frame of reference, and assuming that, for example, the positioner 40 in FIG. 5 has its base (not shown) disposed at x equals 5, z equals 15 in the phantom frame of reference, the second positioner 40' would then have its base (not shown) secured at x equals 5, z equals 15 relative to the patient frame of reference. It should be noted that, in the present invention, the correspondence between coordinates in the phantom frame of reference and the patient frame of reference would not necessarily have to require equivalence between all values. In other words, the coordinates relative to the phantom frame of reference might correspond to coordinates in the patient frame of reference by a simple linear transformation. However, and considering that the frame of reference used for the phantom table 48 may be selected such that there is direct equivalence between coordinates in the two related frames of reference, it is ordinarily advantageous to have this direct equivalence. This avoids the need for even a simple linear transformation to convert the coordinates of the target 51 into values for setting the target portion 28. The coordinates of the target 51 are simply determined from use of the conventional imaging system and the target portion 28 is secured at the same values of coordinates without any transformation or calculations being necessary.

Once the second positioner 40' is secured to the operation table 50, or before it is secured to the table 50, it is fixed in orientation so as to duplicate the position of first positioner 40. In other words, having read the numerous indicia off the various parts of positioner 40, the second positioner 40' is set by using various indicia (not shown) on it so that it has the equivalent position. The tubular portion 40' would then define a stereotactic trajectory which is the equivalent to the trajectory tested on the phantom table 48. The needle 46' may then be disposed in the tubular portion 42' (or a cannula, not shown, disposed therein) and extended through the incision point 52 in the patient's skull and extended to a length corresponding to the depth of insertion used for the needle 46. At that stage, the needle 46' would be in its operation position.

As an alternative to the technique of using a second positioner 40', one could simply move the first positioner 40 from its position on the phantom table 48 to a corresponding position on the patient or operating table 50. By using a single positioner 40 which is moved from the phantom table 48 to the patient table 50, one avoids the need to read indicia on the positioner 40 and set a similar positioner 40' to those same settings. However, one would still insure that the positioner 40 is attached to the patient table 50 such that its base is at a corresponding position to the position which its base had when attached to the phantom table 48. For those purposes, indicia may be disposed upon the phantom table 48 and the patient table 50. Although the transfer of the single positioner 40 is advantageous in that it avoids the need for conforming the position of a second positioner 40', it would require that the positioner 40 and associated parts, such as the target simulator 26, incision simulator 30, and the phantom base (not shown in FIG. 5) would have to be sterilized. Those parts could be made of stainless steel or other known materials commonly used for parts which are sterilizable by steam treatments. Alternately, the parts could be made by other materials suitable for other sterilization procedures.

Use of a single positioner 40 which is moved from the phantom table 48 to the patient table 50 not only avoids the necessity to transfer settings from one positioner to another, but it avoids any minor imprecision which might be caused if there are slight variations in size or shape between the first positioner 40 and the second positioner 40'. However, a first positioner 40 and a second positioner 40' might be advantageous under certain circumstances and imprecision could be minimized by insuring that the manufacturing tolerances of the two positioners were adequately controlled.

Whether one used the two positioner technique having duplicate positioners 40 and 40' or one used a single positioner 40 which is moved between the phantom table 48 and the patient table 50, a single needle 46 might be used. Alternately, and as shown, a first needle or other surgical tool 46 might be used on the phantom table 48 and a second needle or surgical tool 46' would be used on the patient table 50. In that case, the surgical tool or, more specifically, needle 46 for the phantom table 48 might simply be a simulated surgical tool having the shape and/or size, and/or other characteristics corresponding to the actual surgical tool 46'.

Turning now to FIG. 6, a more detailed discussion of the construction of the phantom table 48 and phantom 22 will be presented. The phantom table 48 has an opening 54 extending there through, which opening is disposed between opposite side members 56F and 56S, both of which extend in the z direction, perpendicular to the plane of view of FIG. 6. The opening 54 may simply be a rectangular opening extending within a rectangular frame work having members such as 56F and 56S. The base 24 of phantom 22 may be secured to the table 48 by use of thumb screws such as 58. Although only one thumb screw 58 is shown for securing the base 24 to the table 48, four such thumb screws or other fasteners may be used, one corresponding to each of four corners of the base 24. Each of the thumb screws such as 58 would extend through the base 24 and into a corresponding hole (not separately labeled) in a portion of the table 48 such as 56F.

The base 24 has identical, parallel tracks 38S and 38F (only 38S is shown in FIGS. 6-8, but 38F is shown schematically in FIG. 3). Target track 34 and incision track 36 both extend between the tracks 38S and 38F and are slidable in the x direction along tracks 38S and 38F. FIG. 7 shows how one end of track 34 may include a portion 60P which is shaped to wedge and slide within a mating slot 60S extending substantially along the entire length of the track 38S. The thumb screw 62 extends through a hole in track 34 may be screwed toward track 38S so as to press against a top surface of track 38S and secure track 34 against movement relative to track 38S. Arrangements other than thumb screws might be used to secure track 34 when it is in a desired position. The thumb screw 62 would normally be partially unscrewed to allow movement of track 34 relative to track 38S until track 34 was in the desired position. The end of track 34 opposite that shown in FIG. 7 would have a wedge portion (not shown) mating to a slot of the track 38F and would include a thumb screw such as 62. Likewise, the track 36 would move in tracks 38S and 38F using the same wedge and mating slot type arrangement.

Considering now FIG. 6 in conjunction with FIG. 8, the track 34 has a slot 64 having a target carriage 66 slidably wedged therein (carriage 66 shown in FIG. 6 only). The target carriage 66 is part of the target simulator 26 which also includes a target member or rod 68 having the target portion 28 at its tip. By moving the carriage 66 in the z direction along target track 34, one can move the target portion 28 in the z direction. By moving the track 34 in the x direction along tracks 38S and 38F, one can move the target portion 28 in the x direction. A thumb screw 70 or other arrangement could be used to secure the carriage 66 in its proper position such that its x and z coordinates correspond to the x and z coordinates of the target 50 within the patient (refer back momentarily to FIG. 5).

Referring now to FIG. 6 in conjunction with FIGS. 9 and 10, a cut out slot 72 extends substantially along the lengthwise direction of track 34 and below the slot 64. The cut out slot 72 allows the target rod 68 to be moved up and down as it extends through a hole in carriage 66 (see especially FIG. 10) and through the cut out down until the target portion 28 (FIG. 6 only) has the proper y coordinate whereupon a thumb screw 74 is fastened to lock member 68 in place. The thumb screw 74 as well as the other thumb screws could alternately be various other types of known fasteners.

The construction of the incision simulator 30 will now be discussed with reference to FIG. 6. The incision simulator 30 includes an incision carriage 76 which is movable along track 36. The track 36 would be identical to that described for track 34 and would move along tracks 38S and 38F. The carriage 76 would be identical to the carriage 66. The incision simulator 30 further includes an incision rod or member 78 which is securable at different y locations in the same fashion as target rod 68 was secured relative to target carriage 66. The incision member or rod 78 is preferably a straight rod having an incision portion 80 disposed thereon. An incision pivot sleeve 32 is part of the incision portion.

Figure 12:
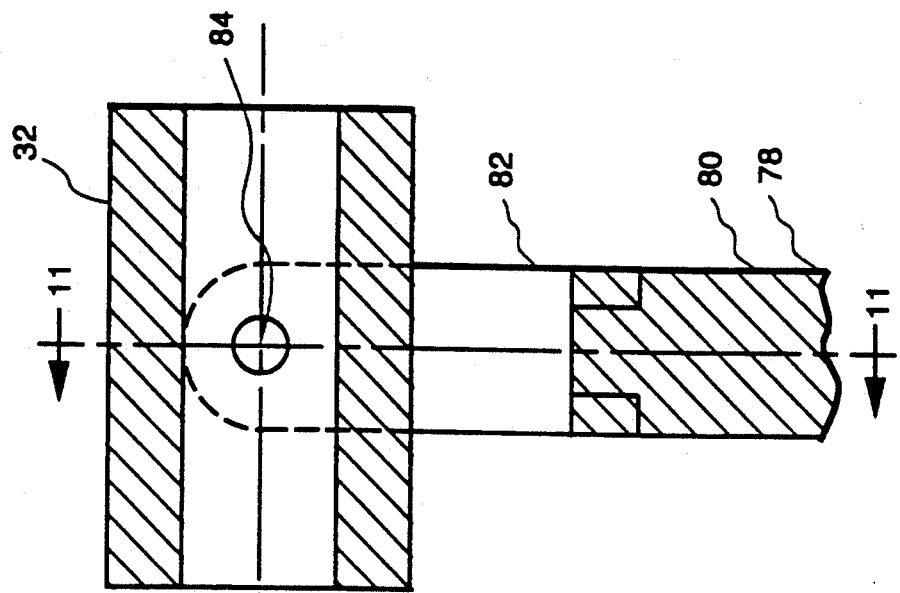
FIG. 12 is a cross section view taken along lines 12—12 of FIG. 11 of the incision pivot and including lines 11—11 illustrating the view used for the cross section of FIG. 11.
Figure 11:
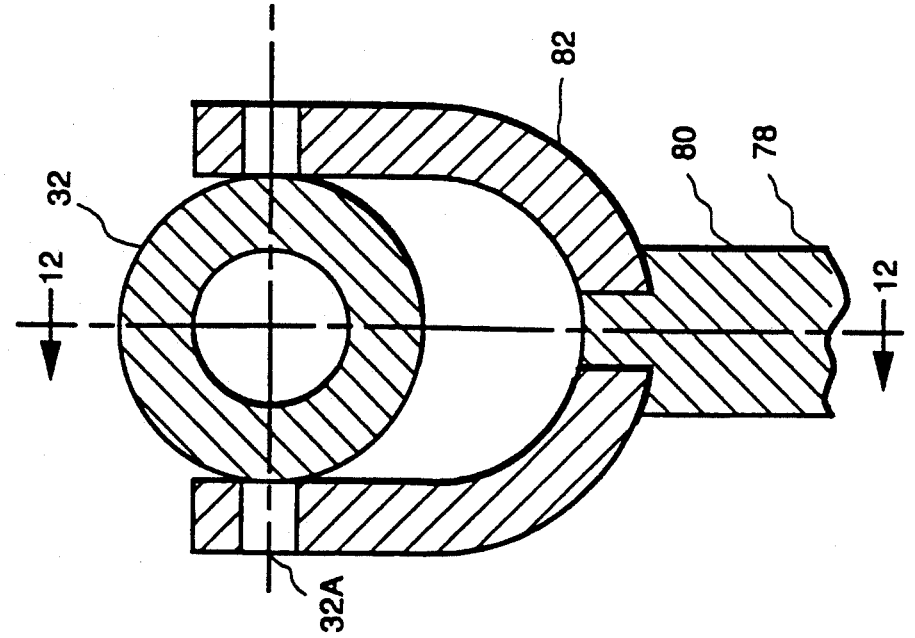
FIG. 11 is a cross section view of an incision pivot.

With reference now to FIGS. 11 and 12, the details of the incision portion 80 disposed at the upper end of incision member 78 will be discussed. The incision portion 80 has a yoke 82 pivotable about an axis extending lengthwise along the cylinder member 78, this direction corresponding to the y axis of FIG. 6. Rotatably mounted on the yoke 82 is the incision pivot sleeve 32 which is rotatable about axis 32A in FIG. 11. Accordingly, the sleeve 32 may rotate about two independent axes, one axis by way of rotation of yoke 82 and the other axis by virtue of rotation of sleeve 32 about axis 32A.

After the carriage 76 is placed at the proper x and z coordinates for the incision point and the rod 78 is moved up or down so that a simulated incision point 84 (FIG. 12 only) has the same x, y, and z coordinates as the planned incision point (52 in FIG. 5 only), rotation of the sleeve 32 does not change the simulated incision point since simulated incision point 84 is at the intersection of the axes of rotation of the sleeve 32.

Figure 13:
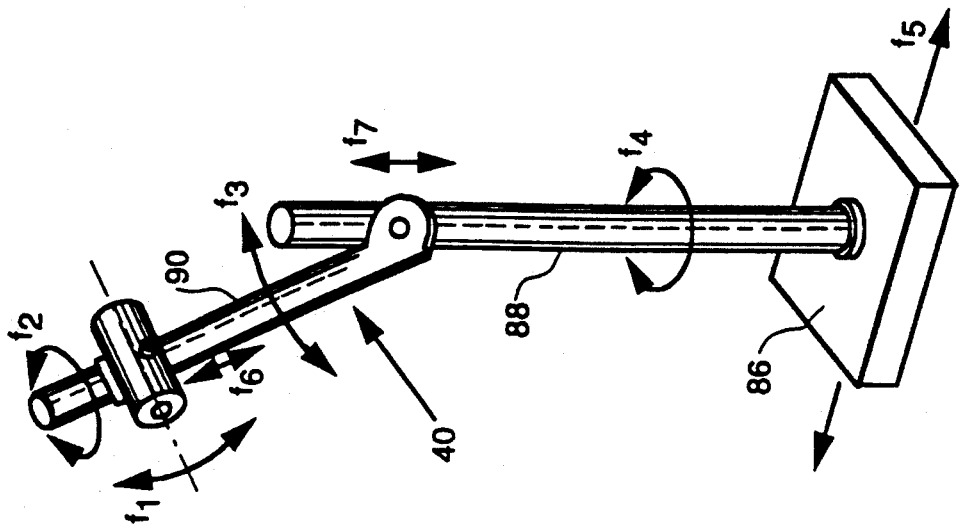
FIG. 13 is a perspective illustrating the degrees of freedom of the positioner.

With reference to FIGS. 6 and 13, the positioner 40 will be discussed. The positioner 40 has a base 86 with a rod 88 mounted thereon. Mounted to the rod 88 is an arm 90 on which the tubular portion 42 is disposed and which will serve as a surgical tool holder. More specifically, the tubular portion 42 may have a cannula (not shown) disposed therein and into which a needle (not shown in FIGS. 6 and 13) may be inserted. The degrees of freedom of the positioner 40 are noted in FIG. 13, each degree of freedom being indicated by the letter f together with a subscript.

Figure 15:
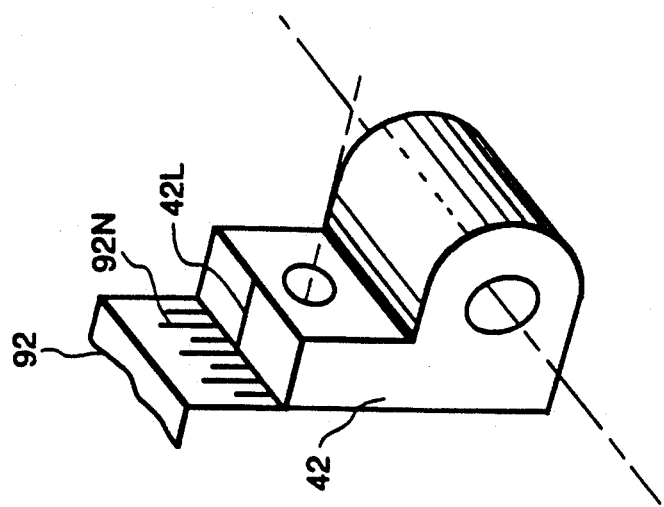
FIG. 15 shows a perspective view of the surgical tool holder.
Figure 14:
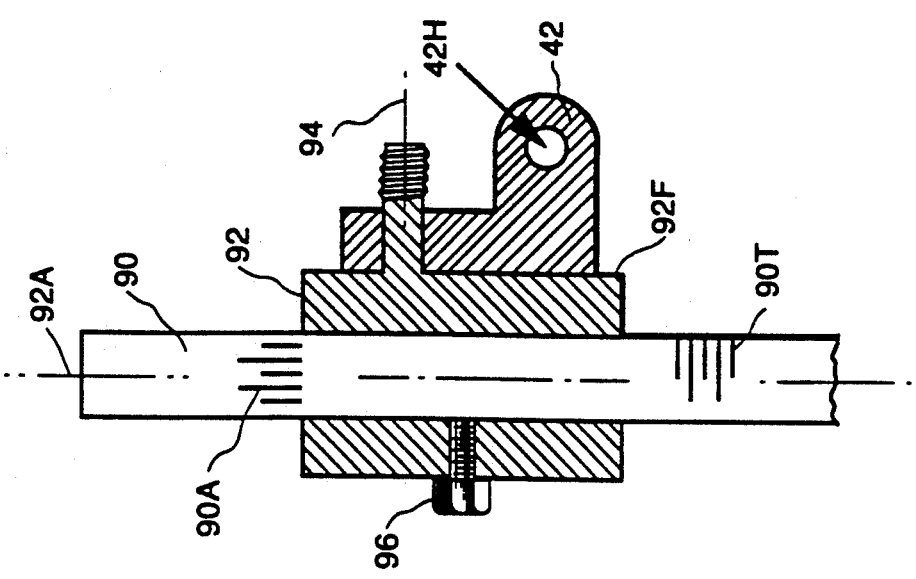
FIG. 14 is a partial cross section illustrating a surgical tool holder of the positioner.

The first and second degrees of freedom may best be considered by reference to FIGS. 13-15. The tubular portion 42 is mounted to a collar 92 and is rotatable about an axis 94 with respect to the collar 92. A wing nut, or other fastener may be used to secure tubular portion 42 relative to the collar 92 when the needle (not shown) or other surgical tool extends through the cylindrical hole 42H in tubular portion 42 at the proper trajectory. Rotation of tubular portion 42 relative to collar 92 corresponds to degree of freedom f1 in FIG. 13. With reference to FIG. 15, an indicator line 42L on the top of portion 42 may line up with various indicia 92N on the collar 92. Although numbers or letters are not shown at the indicia lines 92N, such numbers or letters could be included such that one could determine uniquely the location of tubular portion 42 relative to collar 92. The collar 92 would be generally cylindrical except it would have a flat surface 92F (FIG. 14) facing a corresponding flat surface of the tubular portion 42.

The collar 92 may be rotated about axis 92A to provide degree of freedom $f_2$. A fastener 96 may be used to secure the collar 92 in position. As the collar 92 may be translated or moved along arm 90, this provides a degree of freedom $f_6$. Indicia 90A and indicia 90T may be used respectively to read the angle corresponding to $f_2$ and the translational position corresponding to $f_6$ of the tubular portion 42. Pointers or markers (not shown) on the collar 92 may point to particular ones of the indicia 90A and 90T to provide such readings.

A third rotational degree of freedom $f_3$ is provided by rotation of the arm 90 relative to the rod 88. If desired, the arm 90 may be mounted to rod 88 by using an arrangement similar to that shown in FIG. 14 except that instead of having a tubular portion having hole 42H extending therethrough, the arm 90 would be mounted to a collar similar to collar 92. The collar (not separately shown) used for mounting the arm 90 would provide for a rotational degree of freedom $f_4$ and a translational degree of freedom $f_7$, whereas the mounting of arm 90 on such a collar similar to collar 92 would provide for the rotational degree of freedom $f_3$. Indicia (not shown) could be used to provide readings relative to $f_3$, $f_4$, and $f_7$.

Fasteners such as thumb screw 96 would be used to secure positioner 40 relative to each of its degrees of freedom.

Figure 16:
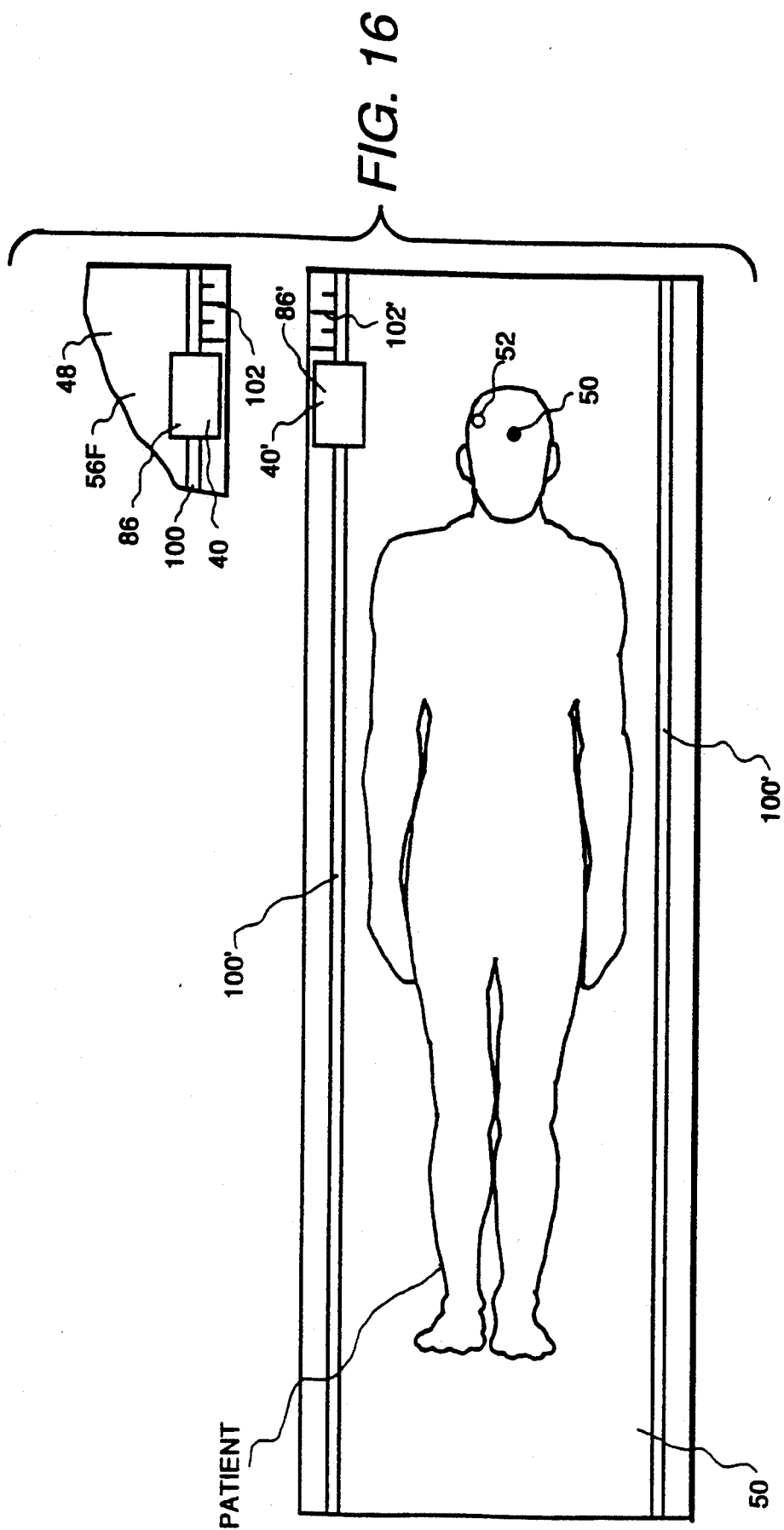
FIG. 16 shows a simplified view of a patient table and adjacent phantom table according to the present invention.

With reference to FIGS. 6, 13, and 16, degree of freedom $f_5$ of the position 40 will be discussed. The positioner 40 may have a wedge portion 86W on its base 86, the wedge portion sliding in a slot 100 such that member 56F may serve as a z axis track. A thumb screw 98 may be used to secure the positioner 40 in a desired location. As shown in FIG. 16, the base 86 of positioner 40 (shown in simplified form) may slide along the track 100 and be secured in a desired position, whereupon the indicia 102 on member 56F of phantom table 48 may be read. If one then wished to move the positioner 40 to the patient or operating table 50, the positioner 40 would be secured in a corresponding z axis track 100' so that the indicia 102' would read the same as the indicia 102 read previously. For ease of illustration, the indicia 102 and 102' have not been shown extending along the length of all of the tracks within the tables 50 and 48. However, it will be appreciated that indicia such as markings together with numbers and/or letters would extend along each of the tracks. Both the patient table 50 and the phantom table 48 would include a z axis track at both sides and one would use the corresponding track when one wished to move the positioner 40 from phantom table 48 to operating table 50.

Instead of moving the positioner 40 from phantom table 48 to operating table 50, one might simply use a separate positioner 40' as previously discussed. The base 86' of such a positioner 40' would then be disposed at the same z axis location along one of the tracks 100' as used for the first positioner 40.

If one was using the technique of transferring a positioner from the phantom table to the operating table, it would not be necessary to include indicia such as the indicia 90A, 90T, and 92N discussed previously with respect to FIGS. 14 and 15 even though such indicia will be helpful in keeping the record of a procedure. However, if one was using the technique of setting a duplicate positioner such as positioner 40' to the same orientation or trajectory as the positioner 40, one would include indicia relative to each degree of freedom on the positioner itself.

Although the arrangements of FIGS. 6 and 16 having used z axis tracks 100 and 100' to allow securing of the positioners 40 and 40', various other arrangements could be used for mounting the positioners to the respective tables. For example, instead of using tracks as a positioner receiver in the tables, one might use a series of holes (not shown) into which the positioners could be bolted or otherwise secured. The positioner receiver on the phantom table 48 and/or patient table 50 may alternately be simply a section of the table having indicia thereon and allowing the positioner to be clamped or otherwise secured thereto.

Although the arrangement of FIG. 6 should be sufficient for most trajectories, the finite extent of the tracks 34 and 36 in the x direction does limit the possible trajectories. Basically, one cannot use this technique for a vertical trajectory (straight along the y axis) or a trajectory which is within a particular angle of vertical. This limitation results from the fact that the track 34 and track 36 cannot be directly above one another. If a surgeon wished to try a trajectory which could not be tested using the phantom 22 of FIG. 6, the patient could be reoriented so that the trajectory was not vertical or close to vertical and the surgeon could use the same planned incision point on the patient without running into a problem in testing the trajectory by use of phantom 22.

An alternate base 24 for the phantom 22 is not illustrated but might be used to minimize any problems in the relatively small percentage of cases where the trajectory would be limited by the extent of the tracks 34 and 36. In particular, such an alternate arrangement might have the tracks 34 and 36 sliding in separate vertically (y axis) offset x tracks.

The tracks and wedge portions fitting in tracks used for the invention should be machined to close tolerance to avoid or minimize positional inaccuracies. If desired, the tracks could have grooves for holding lubricants in known fashion to avoid introduction of positional errors from lubrication.

Although specific constructions have been described herein, it is to be understood that they are for illustrative purposes only. Various modifications and adaptations will be apparent to those of skill in the art. Accordingly, the scope of the present invention should be determined with reference to the claims appended hereto.

What is claimed is:

1. An apparatus for use in stereotactic medical procedures comprising a phantom having a base defining a plane in which perpendicular x and z axes are disposed, a target simulator and an incision simulator, said target simulator being movably positionable at different x, z locations on said base, said target simulator having a target portion which is securable at different y locations along a y axis extending perpendicular to said plane, and wherein x, y, and z axes are orthogonal, said incision simulator being movably mounted to said base for positioning at different x, z locations on said base, sad incision simulator having a member with an incision portion thereon, said incision portion securable at different y locations, and said incision portion having a pivot defining a simulated incision point therein, said pivot being mounted for independent rotation about perpendicular first and second pivot axes, and wherein said pivot is rotatable about said first and second pivot axes without changing the x, y, z coordinates of said simulated incision point, and wherein said pivot is adapted to accommodate a surgical tool therein such that the surgical tool may extend through said pivot to said target portion for determining the proper positioning of the surgical tool for a stereotactic medical procedure.

2. The apparatus of claim 1 wherein the first pivot axis is perpendicular to said plane and said second pivot axis is parallel to said plane.

3. The apparatus of claim 1 wherein said target simulator includes a target carriage mounted to said base for tracked movement along the x and z axes and said incision simulator includes an incision carriage mounted to said base for tracked movement along the x and z axes.

4. The apparatus of claim 1 wherein said base includes at least one x track extending in the x axis and two z tracks extending in the z axis, said z tracks slidably mounted to said x track, and wherein each of said target carriage and incision carriage is slidably mounted to separate ones of said two z tracks.

5. The apparatus of claim 1 further comprising a phantom table having a positioner receiver thereon, said phantom being mounted to said phantom table, and a first positioner mounted to said positioner receiver having a surgical tool holder, said surgical tool holder having a plurality of degrees of freedom, said surgical tool holder adapted to dispose said first positioner in an operation position whereat the surgical tool holder holds a surgical tool so that it extends from the surgical tool holder through the pivot to the target portion.

6. The apparatus of claim 5 wherein said surgical tool holder of said first positioner includes a tube portion rotatable about two perpendicular tube axes.

7. The apparatus of claim 6 wherein said pivot and said tube portion are both cylindrical.

8. A stereotactic system comprising:
a phantom having a base defining a plane in which perpendicular x and z axes are disposed, a target simulator and an incision simulator, said target simulator being movably positionable at different x, z locations on said base, said target simulator having a target portion which is securable at different y locations along a y axis extending perpendicular to said plane, and wherein x, y, and z axes are orthogonal, said incision simulator being movably mounted to said base for positioning at different x, z locations on said base, said incision simulator having a member with an incision portion thereon, said incision portion securable at different y locations, and said incision portion having a pivot defining a simulated incision point therein, said pivot being mounted for independent rotation about perpendicular first and second pivot axes, and wherein said pivot is rotatable about said first and second pivot axes without changing the x, y, z coordinates of said simulated incision point, and wherein said pivot is adapted to accommodate a surgical tool therein such that the surgical tool may extend through said pivot to said target portion for determining the proper positioning of the surgical tool for a stereotactic medical procedure;
a phantom table having a positioner receiver thereon, said phantom being mounted to said phantom table, and a first positioner mounted to said positioner receiver having a surgical tool holder, said surgical tool holder having a plurality of degrees of freedom, said surgical tool holder adapted to dispose said first positioner in an operation position whereat the surgical tool holder holds a surgical tool so that it extends form the surgical tool holder through the pivot to the target portion; and
a patient table adjacent said phantom table and having a second positioner receiver thereon, and wherein said second positioner receiver of said patient table and said first positioner receiver of said phantom table each have indicia adjacent thereto to allow duplication of positioner placement on the patient table and phantom table.

9. A method for stereotactic medical procedures comprising the steps, not necessarily in order, of
positioning a target simulator of a phantom at an $X_t$, $Z_t$ location relative to a base of the phantom, the base defining a plane in which perpendicular x and z axes are disposed;
securing a target portion of the target simulator at a $Y_t$ location corresponding to a y axis extending perpendicular to the plane and where $X_t$, $Y_t$, $Z_t$ correspond respectively to coordinates along the x, y, and z axes of a target within a patient;
positioning an incision simulator of the phantom at an $X_i$, $Z_i$ location relative to the base of the phantom;
securing an incision portion on a member of the incision simulator at a $Y_i$ location,
wherein $X_i$, $Y_i$, and $Z_i$ correspond respectively to coordinates along the x, y, and z axes of a planned incision point on a patient, said incision portion having a pivot defining a simulated incision point wherein, said pivot being mounted for independent rotation about perpendicular first and second pivot axes; placing a surgical tool within the pivot; and rotating the pivot about at least one of the first and second pivot axes such that a tip of the surgical tool touches the target, the pivot being rotatable about said first and second pivot axes without changing the x, y, z coordinates of said simulated incision point.

10. The method of claim 9 further comprising the steps of:

placing a first positioner adjacent the phantom, the first positioner having a surgical tool holder with the surgical tool disposed therein, said surgical tool holder having a plurality of degrees of freedom, wherein said rotating of the pivot is performed with the surgical tool in the pivot and in the surgical tool holder to dispose the first positioner in an operation position whereat the surgical tool extends to the target portion; and securing the first positioner in the operation position.

11. The method of claim 10 wherein the phantom is secured to a phantom table having a z track extending in the z axis and the placing of the first positioner adjacent the phantom is accomplished by securing the first positioner along the z track in the phantom table.

12. The method of claim 10 wherein the securing of the first positioner in its operation position is accomplished by securing a plurality of fasteners, each fastener securing the surgical tool holder against movement relative to at least one of the degrees of freedom.

13. The method of claim 12 further comprising the steps of moving the first positioner from adjacent the phantom to adjacent the patient with the first positioner remaining in the operation position and performing a medical procedure on the patient with the surgical tool holder determining the incision point and target on the patient respectively corresponding to $X_i$, $Y_i$, $Z_i$ and $X_t$, $Y_t$, $Z_t$.

14. The method of claim 13 further comprising rotating a tube portion of the surgical tool holder of the first positioner about at least one tube axis when rotating the pivot.

15. The method of claim 13 further comprising rotating a tube portion of the surgical tool holder of the first positioner about two perpendicular tube axes when rotating the pivot.

16. The method of claim 13 wherein the first and second pivot axes about which the pivot is rotated are respectively perpendicular to the plane and parallel to the plane.

17. The method of claim 12 further comprising the steps of placing a second positioner having a surgical tool holder adjacent a patient with the second positioner in an operation position dependent on the operation position determined by use of the first positioner and performing a medical procedure on the patient with the surgical tool holder of the second positioner determining the incision point and target on the patient respectively corresponding to $X_i$, $Y_i$, $Z_i$ and $X_t$, $Y_t$, $Z_t$.

18. The method of claim 17 further comprising the steps of determining a plurality of settings on the first positioner when it is in its operation position and securing the second positioner in its operation position such that it has the same settings as determined from the first positioner.

19. The method of claim 9 wherein the first and second pivot axes about which the pivot is rotated are respectively perpendicular to the plane and parallel to the plane.

20. The method of claim 9 wherein the steps of positioning the target simulator is accomplished by movement of the target simulator along tracks in the phantom base running along the x and z axes and wherein the step of positioning the incision simulator is accomplished by movement of the incision simulator along tracks in the phantom base running along the x and z axes.

* * * * *